(12) United States Patent
Callahan (10) Patent No.: US 8,869,410 B1
(45) Date of Patent: Oct. 28, 2014

(54) MARKING DEVICE

(71) Applicant: Richard Frederick Callahan, Downers Grove, IL (US)

(72) Inventor: Richard Frederick Callahan, Downers Grove, IL (US)

(*) Notice: Subject to any disclaimer, the term of this patent is extended or adjusted under 35 U.S.C. 154(b) by 0 days.

(21) Appl. No.: 14/144,476

(22) Filed: Dec. 30, 2013

(51) Int. Cl.
*A61C 19/04* (2006.01)
*B25H 7/04* (2006.01)
*A61C 7/14* (2006.01)

(52) U.S. Cl.
CPC .................................. *A61C 7/146* (2013.01)
USPC ..................... 33/41.4; 33/42; 33/514; 433/75

(58) Field of Classification Search
USPC ........... 33/41.4, 42, 41.1, 41.5, 41.6, 44, 513, 33/514; 433/75, 72
See application file for complete search history.

(56) References Cited

U.S. PATENT DOCUMENTS

| 2,583,679 A | | 1/1952 | Boston | |
|---|---|---|---|---|
| 2,588,658 A | * | 3/1952 | Plotnik | 33/42 |
| 2,659,980 A | | 11/1953 | Dunn | |
| 2,675,617 A | * | 4/1954 | Goldman et al. | 33/18.1 |
| 2,867,042 A | | 1/1959 | Sutton | |
| 3,164,906 A | * | 1/1965 | Andaloro | 33/41.4 |
| 3,191,295 A | * | 6/1965 | Falk | 30/2 |
| 3,421,223 A | | 1/1969 | Stark | |
| 4,590,677 A | | 5/1986 | Kopp | |
| 4,725,228 A | * | 2/1988 | Andrews | 433/3 |
| 4,850,864 A | * | 7/1989 | Diamond | 433/3 |
| 5,197,195 A | * | 3/1993 | Aikens | 30/293 |
| 5,312,248 A | * | 5/1994 | Zandkarimi | 433/3 |
| 6,418,631 B1 | * | 7/2002 | Ramsthaler | 33/41.4 |
| 6,726,472 B2 | * | 4/2004 | Kuhn | 33/514 |
| 6,736,637 B2 | | 5/2004 | Bond | |
| D584,353 S | | 1/2009 | Schreff et al. | |
| 7,837,464 B2 | | 11/2010 | Marshall | |
| D639,854 S | | 6/2011 | Canizio, Sr. | |
| 8,021,150 B2 | | 9/2011 | Fuentevilla | |
| RE43,364 E | | 5/2012 | Marshall | |
| 2005/0130095 A1 | | 6/2005 | Raby et al. | |
| 2006/0242849 A1 | * | 11/2006 | Fogal et al. | 33/42 |
| 2007/0031774 A1 | | 2/2007 | Cinader, Jr. et al. | |
| 2008/0145811 A1 | | 6/2008 | Diers et al. | |
| 2009/0155739 A1 | | 6/2009 | McLeod | |
| 2012/0311877 A1 | | 12/2012 | Manohar | |

FOREIGN PATENT DOCUMENTS

GB          2 380 164 A    2/2003

* cited by examiner

*Primary Examiner* — Christopher Fulton
(74) *Attorney, Agent, or Firm* — Swift & Swift; Stephen Christopher Swift (57) ABSTRACT

A marking device, designed to mark teeth, to position orthodontic brackets at an optimum level (though it can also be used to mark other things). The invention also relates to a method of marking teeth using the device. The device comprises one or more elongated rectangular metal plates. At each end of each plate is a "leg" that extends downward, with a "foot" covered by plastic. Cylindrical "arms" extend from both sides of each leg at right angles to the plate. Pencil lead (graphite) holders pass through the bars on each side of the plate, so that the pencil leads extend vertically downward and parallel to the plate. Knobs above the holders can be rotated to move the pencil lead up or down. Near each end of each plate, the distance of the pencil lead from the foot is marked in millimeters. Pencil marks aid in placing the orthodontic brackets.

20 Claims, 15 Drawing Sheets

MARKING DEVICE

BACKGROUND OF THE INVENTION

1. Field of the Invention

The present invention relates to marking devices and methods, especially for teeth.

2. Description of the Prior Art

There are numerous prior inventions of marking devices and methods, but none that are equivalent to the present invention.

U.S. Pat. No. 2,583,679, issued on Jan. 29, 1952, to Benjamin P. Boston, discloses a measuring instrument and marker combined, including a pencil holder attached to the end of a flat rectangular leg. The instant invention is distinguishable, in that it has pencil lead holders on opposite sides and ends of the rectangular plate.

U.S. Pat. No. 2,659,980, issued on Nov. 24, 1953, to Joseph W. Dunn, discloses an adjustable marking rule, with flat "tongues" that extend downward and a sliding marker. The instant invention is distinguishable, in that it has pencil lead holders that extend downward in fixed positions at ends of the rectangular plate.

U.S. Pat. No. 2,867,042, issued on Jan. 6, 1959, to Dozier A. Sutton, discloses geometrical instruments, having flat rectangular portions from which extend downwards a pointed member and a ball point marker, rather than the pencil lead holders of the instant invention.

U.S. Pat. No. 3,421,223, issued on Jan. 14, 1969, to Marvin M. Stark, discloses a tooth marking method and means, in which spots on areas of the teeth are marked by the patient biting down on a pad, rather than lines being drawn on sides of the teeth, as in the instant invention.

U.S. Pat. No. 4,590,677, issued on May 27, 1986, to Paul J. Kopp, discloses an alignment gauge for a scriber tool, with a scribing needle extending from one end of a rectangular portion, rather than a pencil lead holder, as in the instant invention.

U.S. Pat. No. 6,736,637, issued on May 18, 2004, to James A. Bond, discloses a pre-marked orthodontic arch wire, in which the marks are on the wire, rather than on the teeth, as in the instant invention.

U.S. Pat. No. 7,837,464, issued on Nov. 23, 2010, to Michael Craig Marshall, discloses a method for determining bracket locations on electronic models of teeth, using virtual marking, rather than physical marking, as in the instant invention.

U.S. Pat. No. 8,021,150, issued on Sep. 20, 2011, to Roberto Carrillo Fuenteville, discloses a method for dental implant placement, using a grid, rather than marking the teeth, as in the instant invention.

U.S. Reissued Pat. No. RE43,364, reissued on May 8, 2012, to Michael Craig Marshall, discloses a method and apparatus using a scanned image for marking bracket locations, in which a model of teeth is physically marked, rather than the actual teeth themselves, as in the instant invention.

U.S. Design Pat. No. D584,353, issued on Jan. 6, 2009, to David J. Schreff and Donna J. Lindsay, discloses a design for a holder for writing or drawing instruments, in which the instruments are held between two rectangular plates, rather than along the sides of a plate, as in the instant invention.

U.S. Design Pat. No. D639,854, issued on Jan. 14, 2011, to Patrick A. Canizio, Sr., discloses a design for a scriber, in which a writing instrument extends through one leg that is movably attached to a rectangular ruler, rather that alongside the leg as in the instant invention.

U.S. Patent Application Publication No. 2005/0130095, published on Jan. 16, 2005, to Richard A. Raby, Oliver L. Puttler and Nicholas A. Stark, discloses a method of orienting an orthodontic appliance to a tooth, involving hypothetical reference lines or rays, rather than physical graphite marks on the teeth, as in the instant invention.

U.S. Patent Application Publication No. 2007/0031774, published on Feb. 8, 2007, to David K. Cinader, Jr. et al., discloses registering physical and virtual tooth structures with markers, in which markers are placed on teeth, but the markers are not pencil lines, as in the instant invention.

U.S. Patent Application Publication No 2008/0145811, published on Jun. 19, 2008, to Nelson R. Diers, discloses a device, method and kit for determining orthodontic dimensions, in which the marks are on a transparent ruler, rather than on the teeth themselves, as in the instant invention.

U.S. Patent Application Publication No. 2009/0155739, published on Jun. 18, 2009, to Neil Stewart McLeod, discloses a dental contact adjustment tool, which makes graphite marks on teeth, but is not designed for making straight lines on teeth, as in the instant invention.

U.S. Patent Application Publication No. 2012/0311877, published on Dec. 13, 2012, to Raghunath Manohar, discloses a marking gauge, in which marking pins extend through, rather than alongside a scribing bar, as in the instant invention.

British Patent No. 2 380 164, published on Apr. 2, 2003, to William Hale and Mark Clarke, discloses a circle scribing and marking tool, in which pencils pass through a scribing plate, rather than alongside, as in the instant invention.

None of the above inventions and patents, taken either sing or in combination, is seen to describe the instant invention as claimed.

SUMMARY OF THE INVENTION

The present invention is a marking device, designed to mark teeth, to position orthodontic brackets at an optimum level (though it may also be used to mark other things). The invention also relates to a method of marking teeth using the device. The device comprises one or more elongated rectangular metal plates. At each end of each plate is a "leg" that extends downward, with a rest or "foot" covered by plastic. Cylindrical bars or "arms" extend from both sides of each leg at right angles to the plate. Pencil lead (graphite) holders pass through the bars on each side of the plate, so that the pencil leads extend vertically downward and parallel to the plate. Knobs above the holders can be rotated to move the pencil lead up or down. Near each end of each plate, the distance of the pencil lead from the foot is marked in millimeters. Thus, if the distance marked is 4.5 millimeters, when the foot is placed against an incisal portion of the teeth, the pencil lead will mark a line on the teeth 4.5 millimeters from the incisal portion, to aid in placing the orthodontic brackets at that distance on the teeth. Different distances may be marked with different ends of one or more plates.

Accordingly, it is a principal object of the invention to provide an apparatus for marking teeth for placement of orthodontic brackets.

It is another object of the invention to provide a method of marking teeth for placement of orthodontic brackets.

It is a further object of the invention to provide an apparatus for marking objects.

Still another object of the invention is to provide a method of marking objects.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention a marking device, designed primarily to mark teeth for the proper placement of orthodontic brackets, but which may also be used for other things. The invention also comprises a method of using the device.

Figure 1:
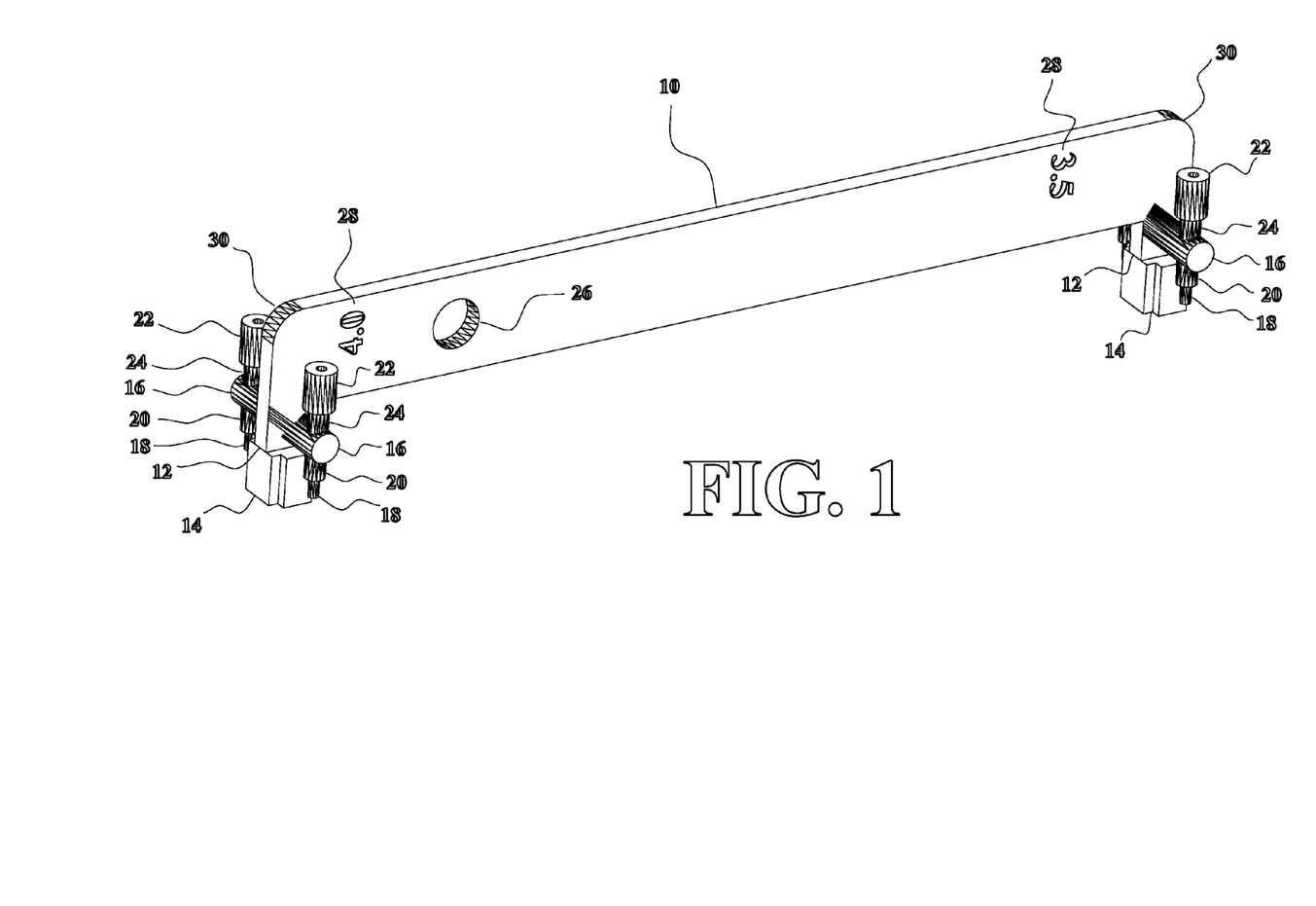
FIG. 1 is a perspective view of the first preferred embodiment of the invention.

FIG. 1 is a perspective view of the first preferred embodiment of the invention, showing the elongated plate 10, which is preferably made of metal. Legs 12 extend downward from each end of the plate. The legs are at right angles to the plate, and coplanar with the plate. At the end of each leg there is a rest or foot 14, which is preferably made of plastic or other material softer than the plate, that can rest comfortably against teethe. Arms 16 extend in opposite directions from each end of the plate, at right angles to the plate and the legs. Pencil "leads" 18 can be retained in pencil lead holders 20 passing through each arm. Knobs 22 can rotate on screw threads 24 on the portions of the pencil lead holders above the arms to adjust the position of the pencil leads. (Alternatively, pens or other writing implements may be substituted for the pencil leads.) A hole 26 at one end of the plate enables it to be retained on a hook.

Figure 2:
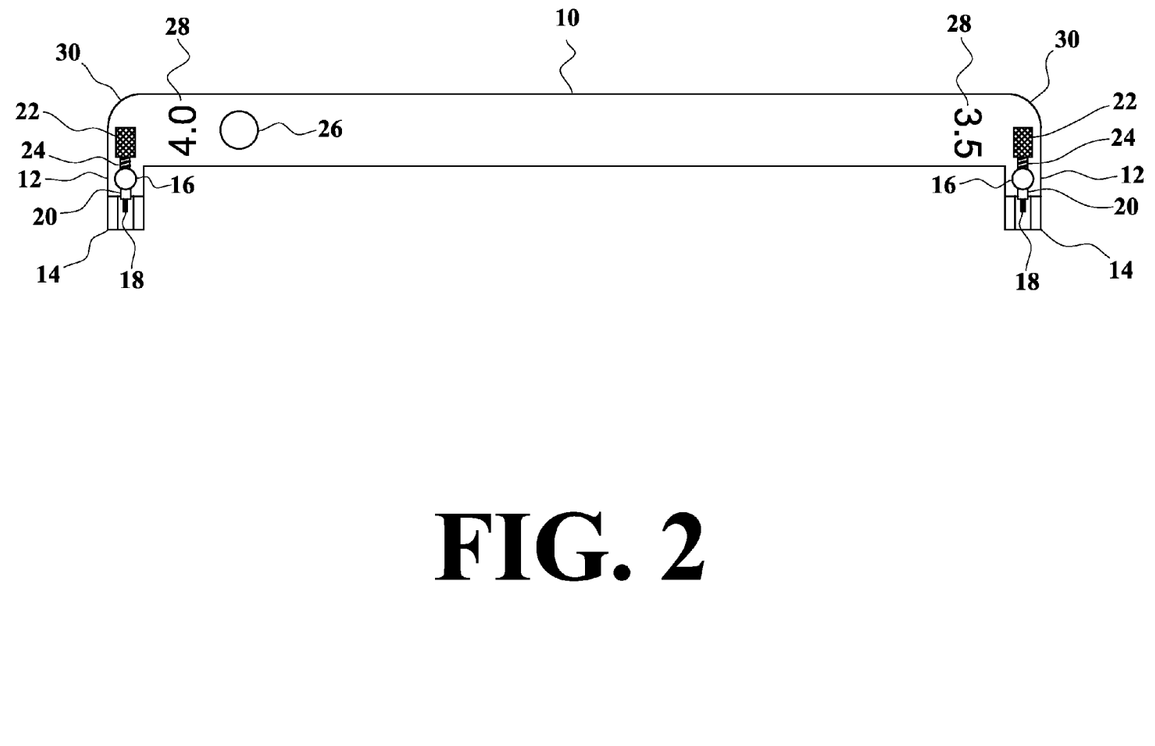
FIG. 2 is a front elevational view of the first preferred embodiment of the invention.
Figure 3:
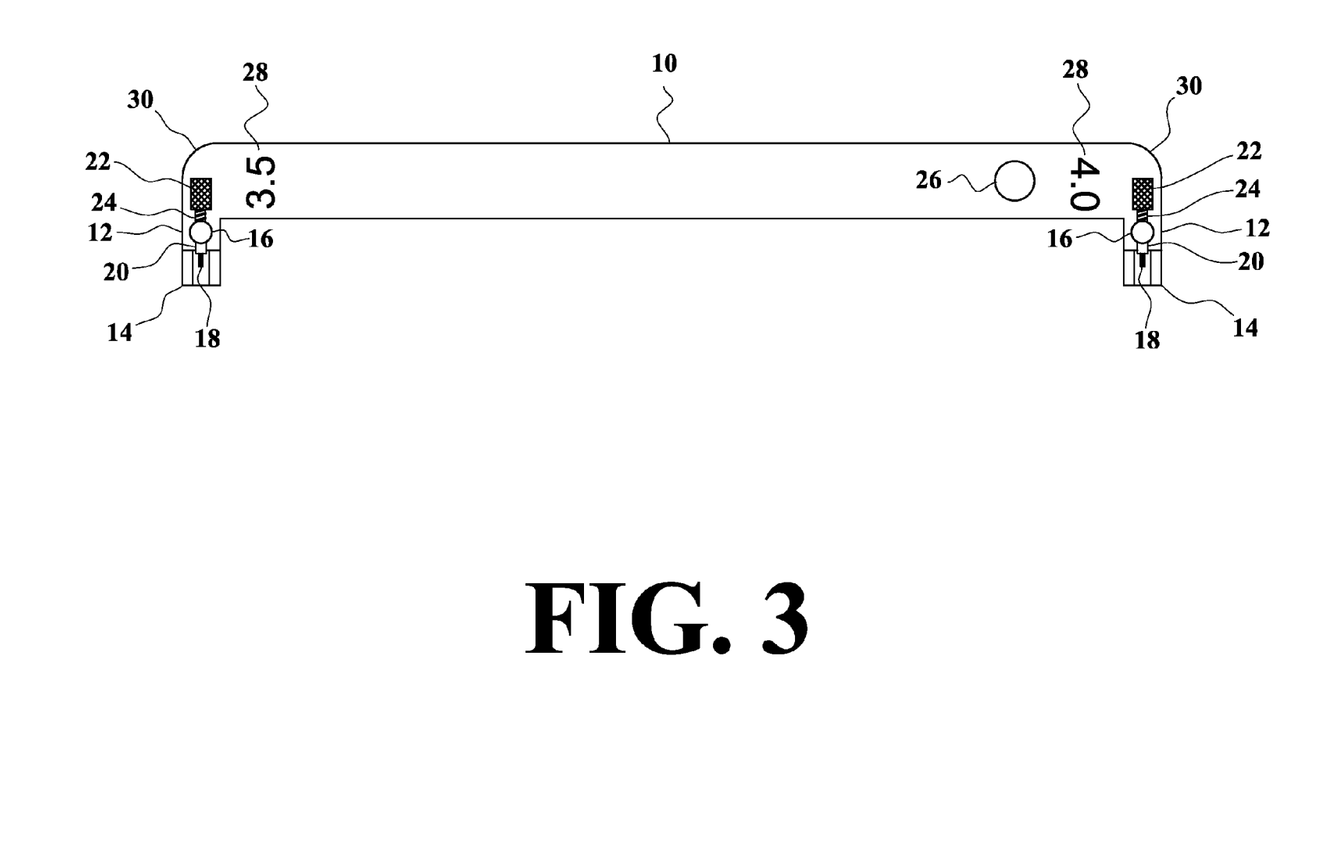
FIG. 3 is a rear elevational view of the first preferred embodiment of the invention.

FIG. 2 is a front elevational view of the first preferred embodiment of the invention, showing the indicia 28 marked on the plate adjacent to each pencil lead holder, giving the distance of the axis of each pencil lead holder from the closest side of the foot adjacent to the pencil lead holder, preferably in millimeters. The upper corners 30 of the plates are preferably rounded. FIG. 3 is a rear elevational view of the first preferred embodiment of the invention, which is the same as the front view, except the position of the indicia 28 and hole 26 are reversed. There may be two or more plates, with different distances marked by the indicia. When there are a plurality of the plates, they may be made of metals with different colors to avoid confusion, e.g., a first plate may be made of stainless steel, and a second plate may be made of brass.

Figure 4:
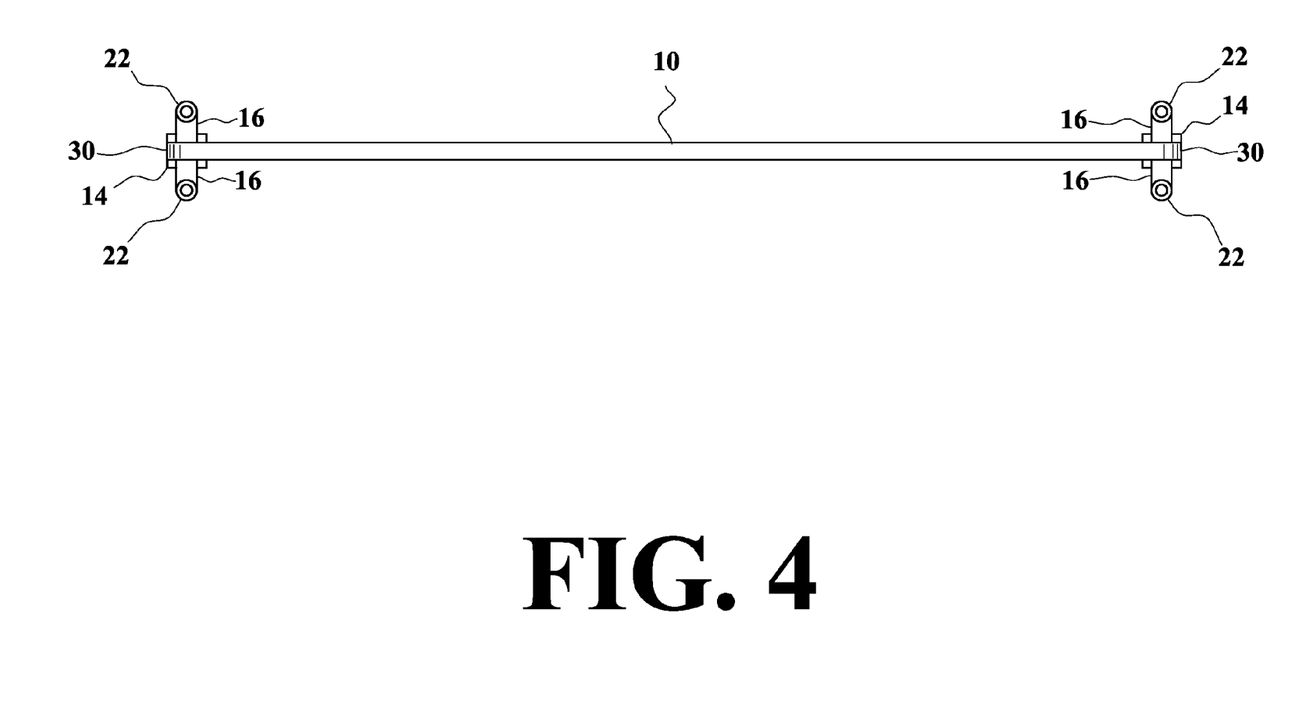
FIG. 4 is a top plan view of the first preferred embodiment of the invention.
Figure 5:
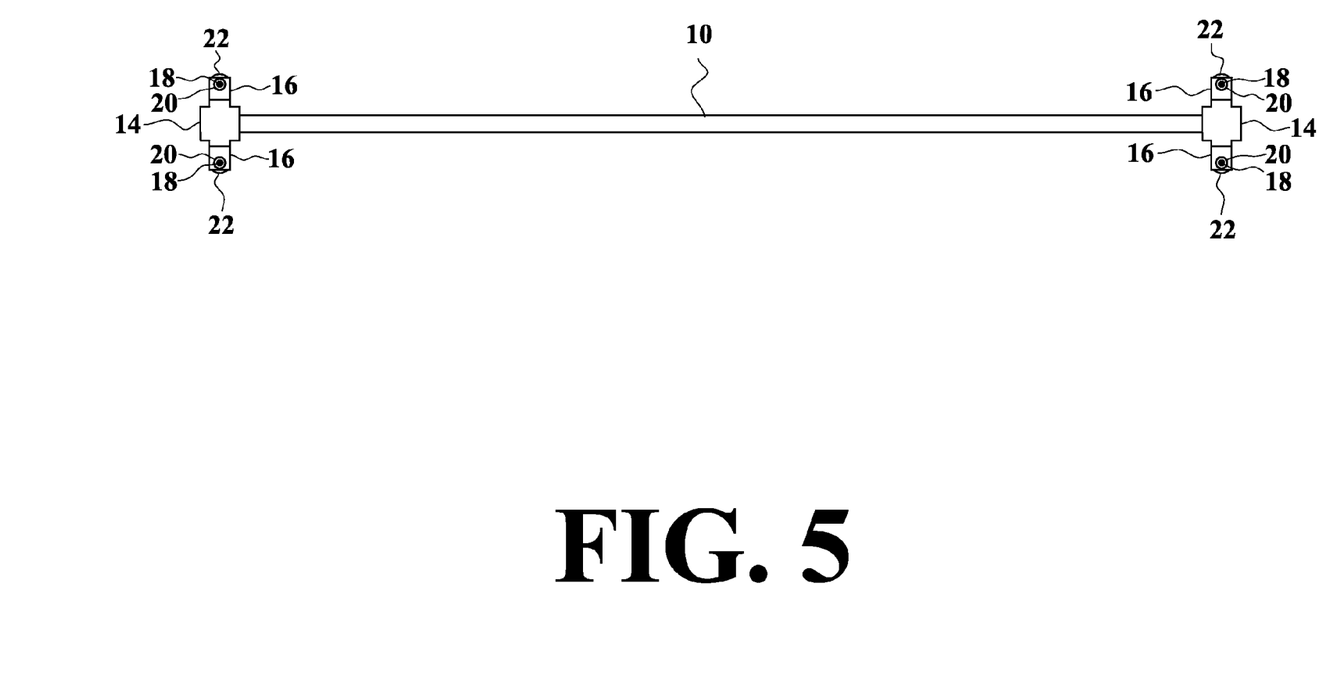
FIG. 5 is a bottom plan view of the first preferred embodiment of the invention.
Figure 6:
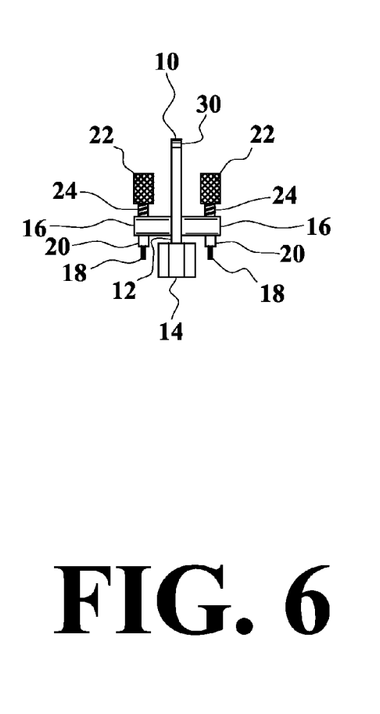
FIG. 6 is a side elevational view of the first preferred embodiment of the invention, with the left and right side views being identical.

FIG. 4 is a top plan view of the first preferred embodiment of the invention. FIG. 5 is a bottom plan view of the first preferred embodiment of the invention. FIG. 6 is a side elevational view of the first preferred embodiment of the invention, with the left and right side views being identical. Each leg passes between two of the writing implements.

Figure 7:
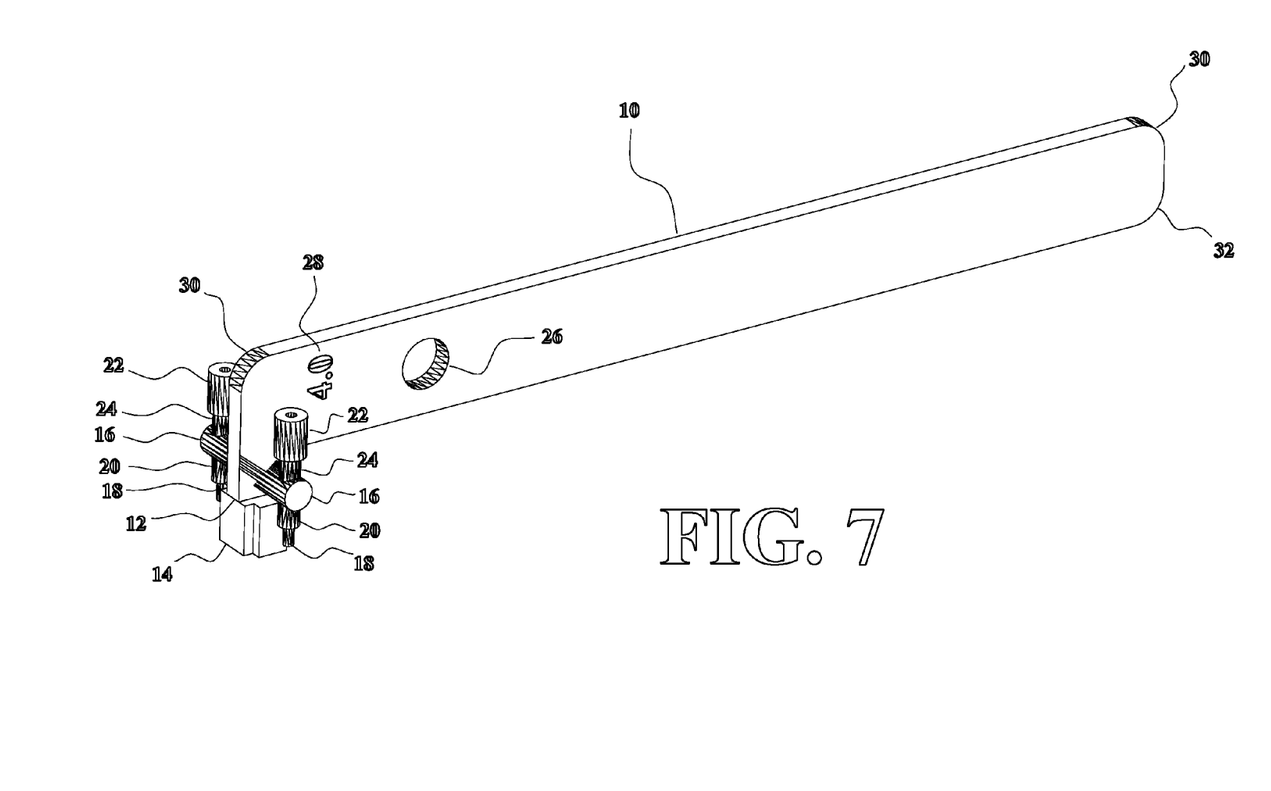
FIG. 7 is a perspective view of the second preferred embodiment of the invention.
Figure 8:
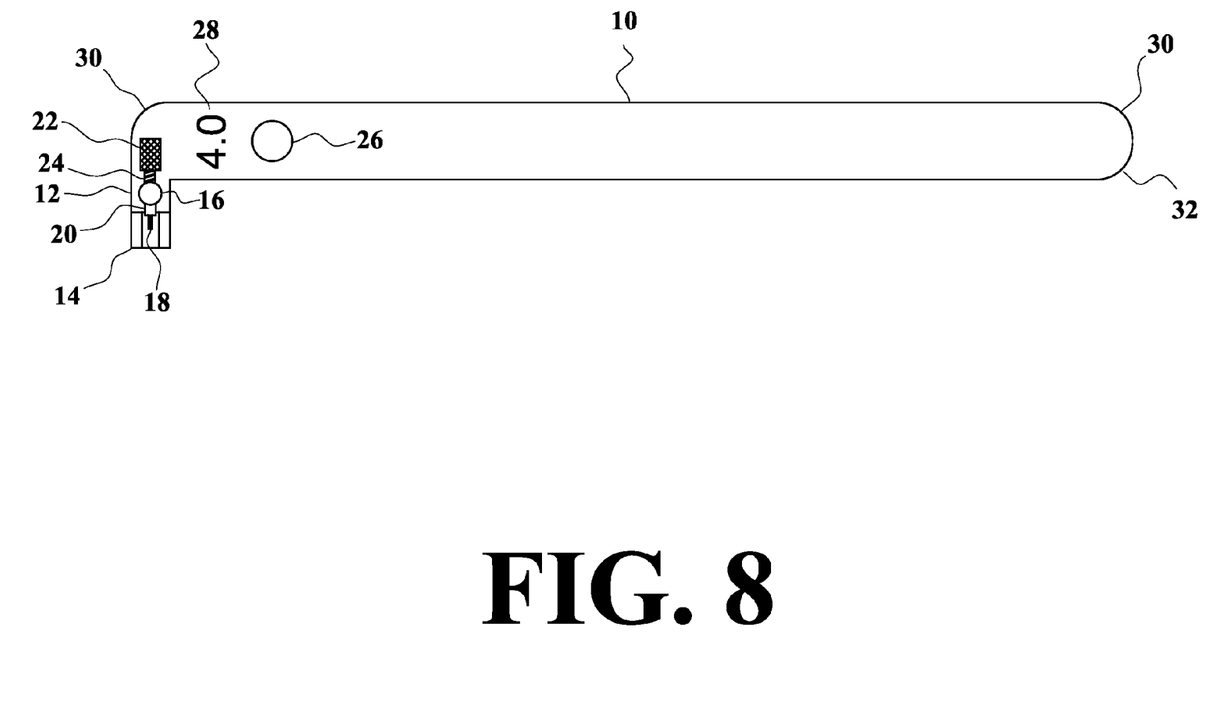
FIG. 8 is a front elevational view of the second preferred embodiment of the invention.
Figure 9:
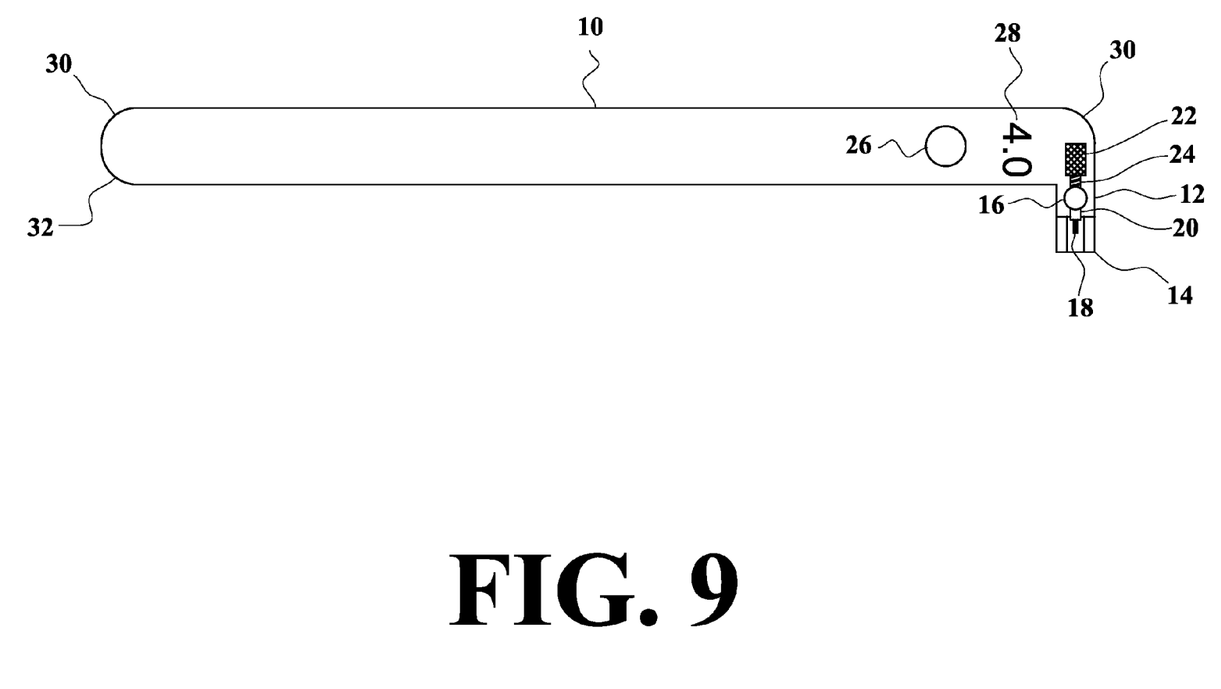
FIG. 9 is a rear elevational view of the second preferred embodiment of the invention.
Figure 10:
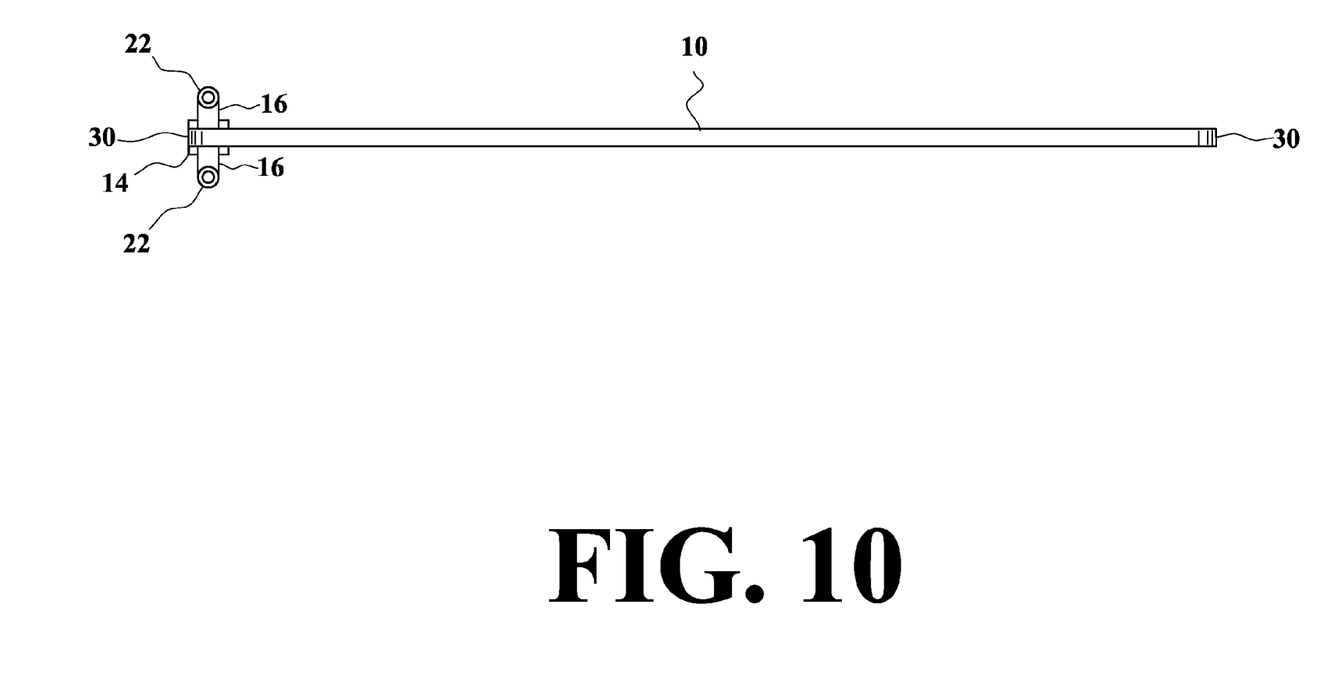
FIG. 10 is a top plan view of the second preferred embodiment of the invention.
Figure 11:
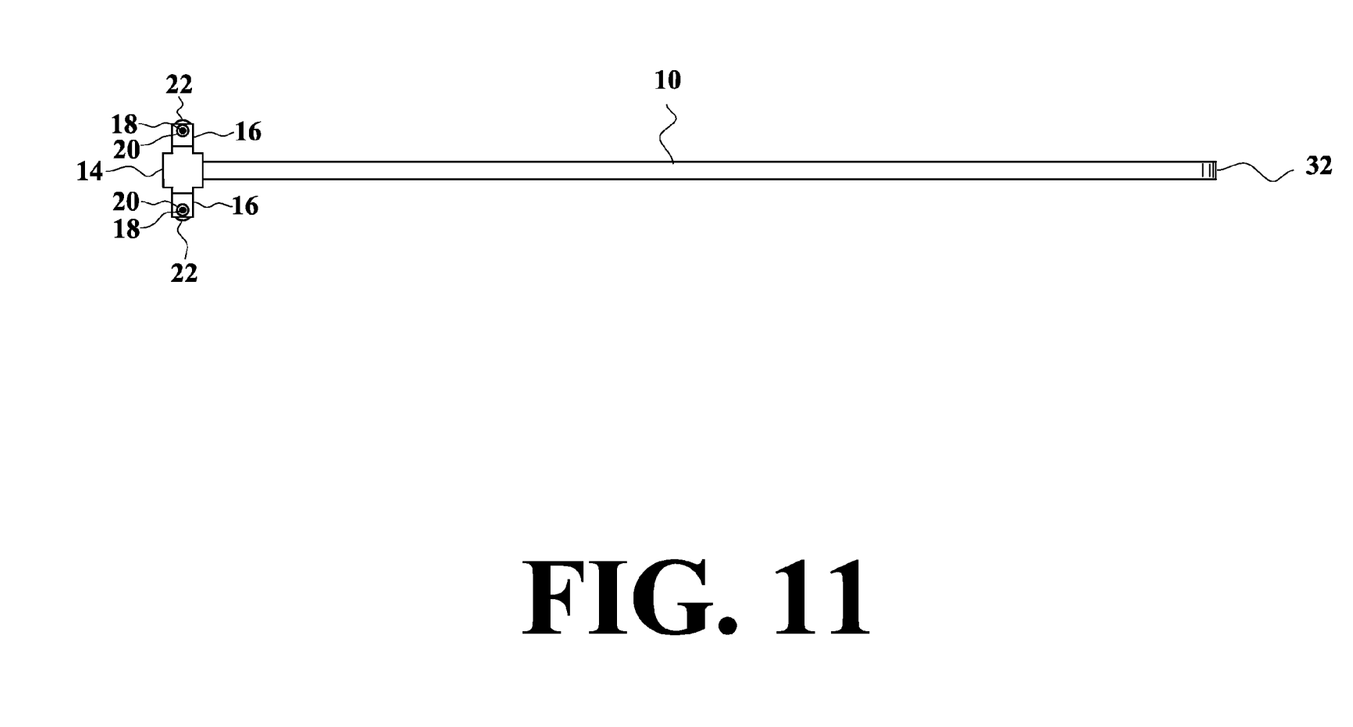
FIG. 11 is a bottom plan view of the second preferred embodiment of the invention.
Figure 12:
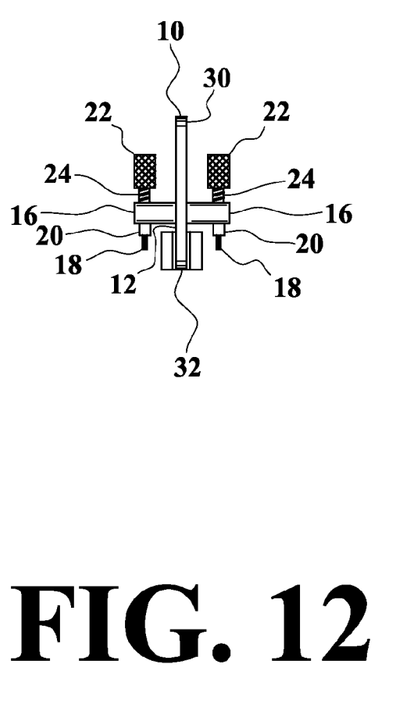
FIG. 12 is a right side elevational view of the second preferred embodiment of the invention.

FIG. 7 is a perspective view, of the second preferred embodiment of the invention. In the second preferred embodiment of the invention, there are only two pencil lead holders 20 or writing implements, at one end of the plate 10, on opposite sides of the plate. In the second preferred embodiment, there is only one leg extending from the same end of the plate as the writing implements, said leg being at right angles to the plate and coplanar with the plate, with the leg passing between the writing implements. There is a single foot 14 at the end of the leg away from the plate, said foot being made of a softer material than the plate. FIG. 8 is a front elevational view of the second preferred embodiment of the invention, showing the lower rounded corner 32 on the side of the plate opposite the writing implements. FIG. 9 is a rear elevational view of the second preferred embodiment of the invention. FIG. 10 is a top plan view of the second preferred embodiment of the invention. FIG. 11 is a bottom plan view of the second preferred embodiment of the invention. FIG. 12 is a right side elevational view of the second preferred embodiment of the invention, with the left side elevational view being identical the that in FIG. 6.

Figure 13:
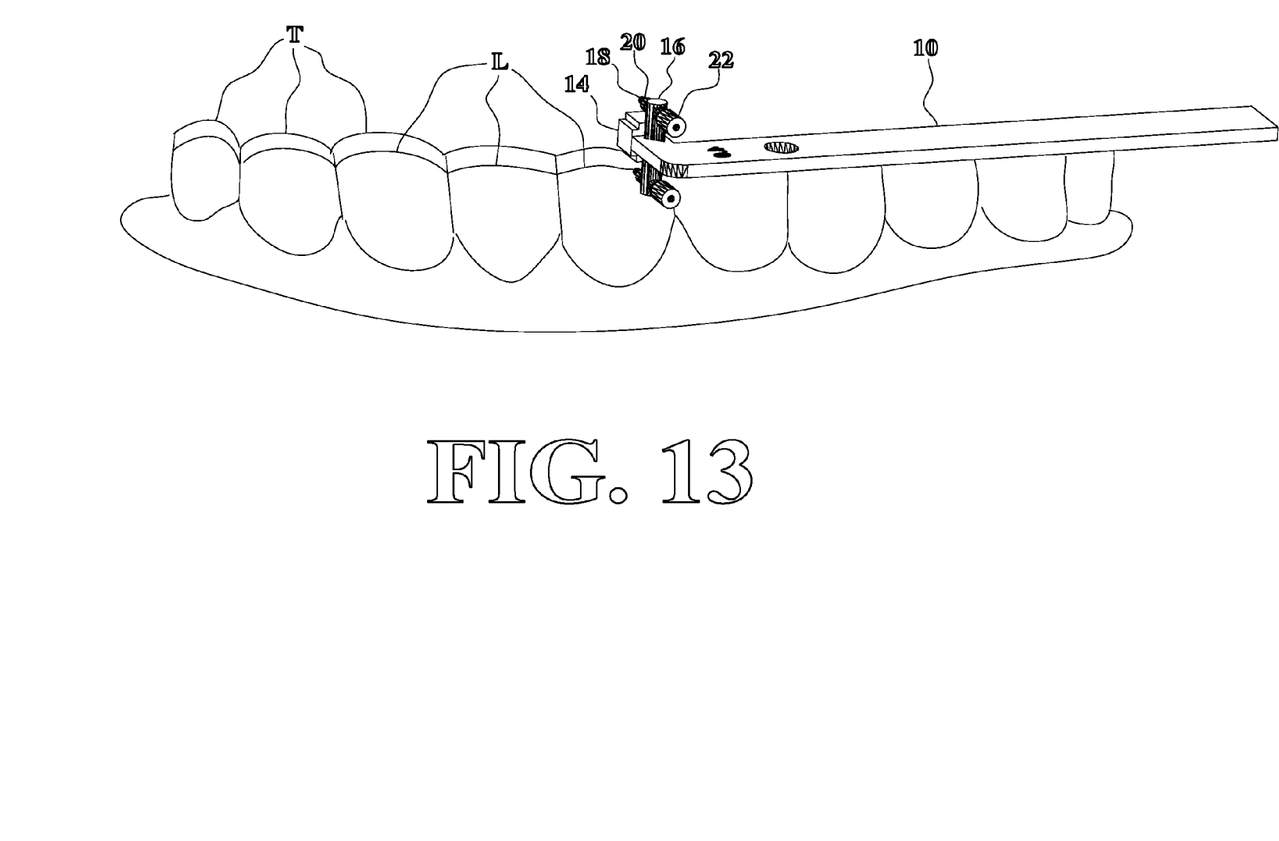
FIG. 13 is an environmental view of either preferred embodiment of the invention, showing it being used mark teeth.

The invention also comprises a method including the steps of: (a) grasping a flat plate with a plurality of writing implements parallel to the plate; (b) placing an extension from the flat plate against an object; and (c) pulling one of the writing implements across the object using the flat plate, marking the object. FIG. 13 is an environmental view of either preferred embodiment of the invention, wherein the object is a tooth T, showing it being used to mark teeth with a line L.

Figure 14:
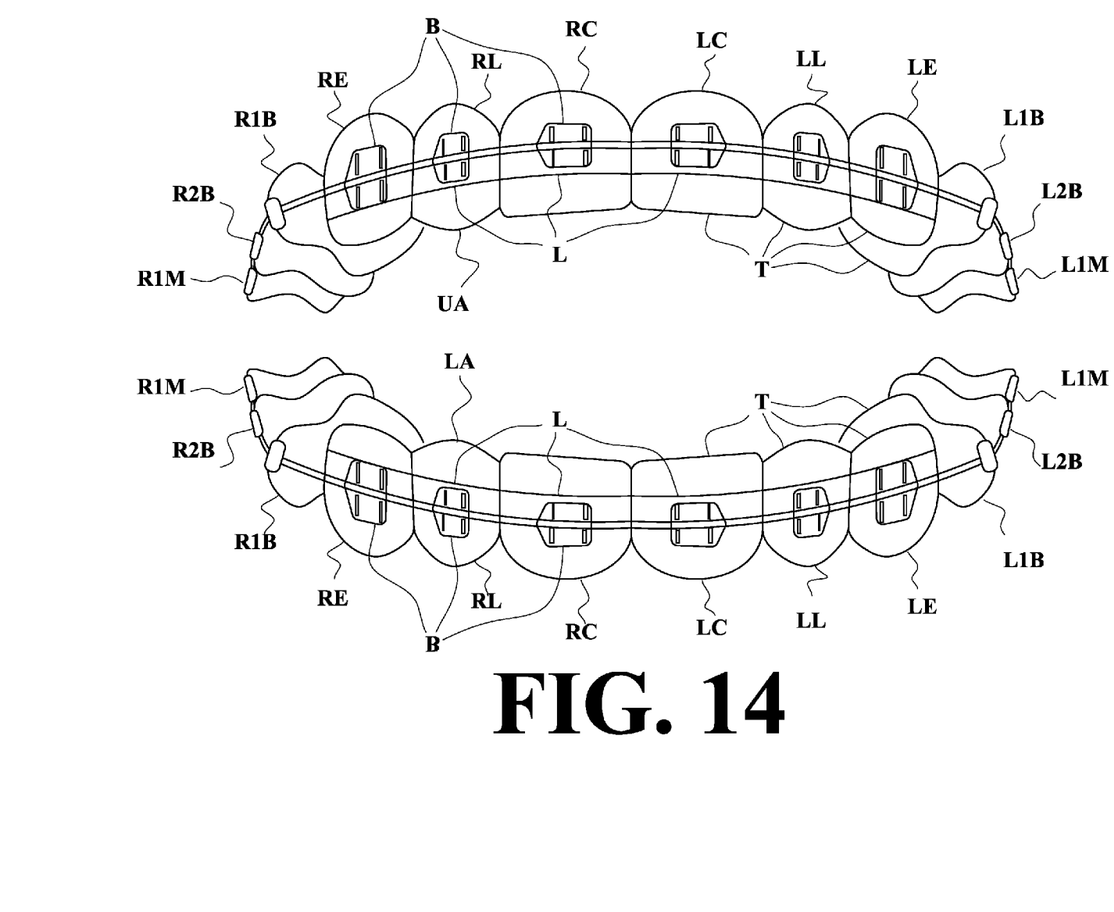
FIG. 14 shows the mark made on teeth using the invention, and the brackets of orthodontic braces placed along the line.

FIG. 14 shows the lines L marked on teeth T using the invention, and the brackets B of orthodontic braces placed along the line. Shown are the teeth of the Maxillary Arch or Upper Arch UA, and the teeth of the Mandibular Arch or Lower Arch LA. The permanent human teeth on each jaw are classified as follows:

Anterior Teeth
   Incisors
      Central
         Left Central LC
         Right Central RC
      Lateral
         Left Lateral LL
         Right Lateral RL
   Cuspid (or Canine or Eye) Teeth
      Left Cuspid LE

```
Right Cuspid RE
Posterior Teeth
  Bicuspid Teeth
    First Bicuspids
      Left First Bicuspid L1B
      Right First Bicuspid R1B
    Second Bicuspids
      Left Second Bicuspid L2B
      Right Second Bicuspid R2B
  Molars
    First Molars
      Left First Molar L1M
      Right First Molar L2M
    Second Molars (not shown)
    Third Molars (Wisdom Teeth) (not shown)
```

The optimum placement of the line on each tooth is measured from the incisal or biting edge of each tooth, which is at the bottom on the upper jaw, and at the top on the lower jaw. For the teeth of the upper jaw, the optimum placement of the line is generally four millimeters from the incisal edge of each tooth, except on the lateral incisors (LL and RL), where it is 3.5 millimeters, and on the cuspids (LE and RE), where it is 4.5 millimeters. For the upper arch, the lower edges of the brackets B should be placed on the line. For the teeth of the lower jaw, the optimum placement of the line is generally four millimeters from the incisal edge of each tooth, except on the cuspids (LE and RE), where it is 4.5 millimeters. For the lower arch, the upper edges of the brackets B should be placed on the line.

Figure 15:
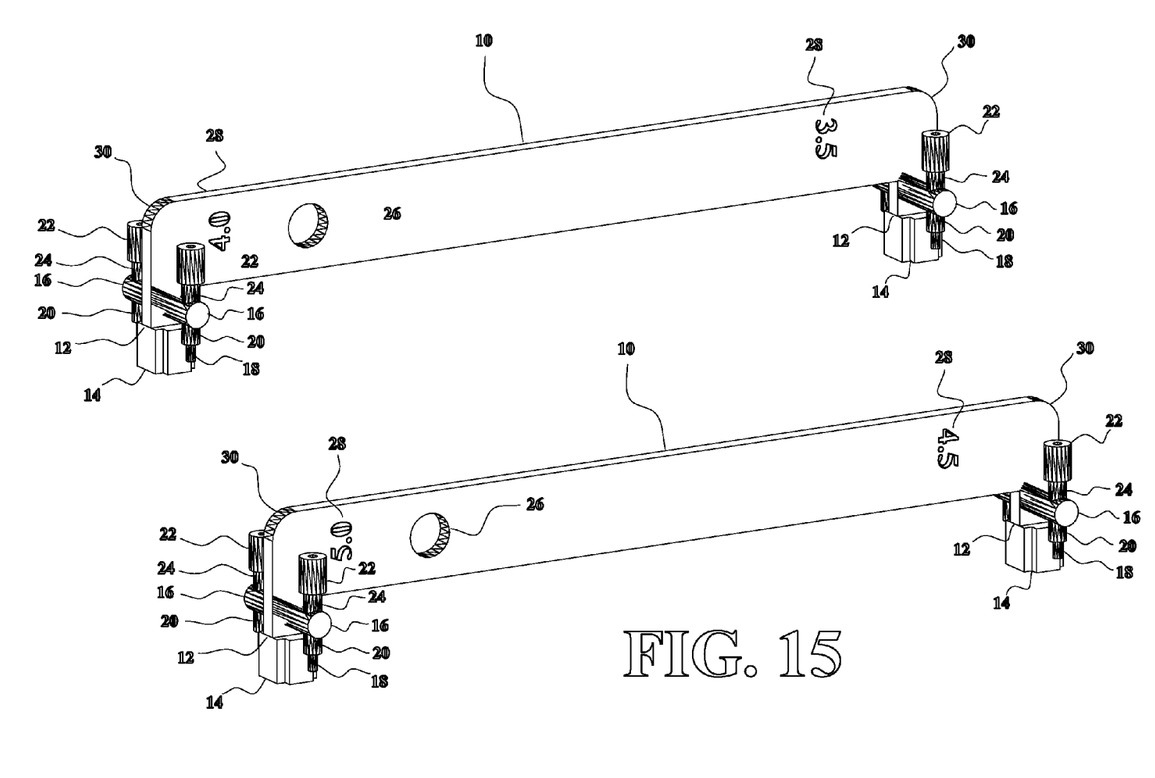
FIG. 15 shows a pair of the plates in the first preferred embodiment of the invention.

The invention will normally be sold as a pair of plates, as shown in FIG. 15, with the upper plate, having ends marking teeth 3.5 and 4.0 millimeters from the incisal edge of the teeth, and the lower plate having ends marking teeth 4.5 and 5.0 millimeters from the incisal edge of the teeth, as indicated by indicia 26.

It is to be understood that the present invention is not limited to the preferred embodiments described above, but encompasses any and all embodiments within the scope of the following claims.

I claim:

1. A marking device, comprising:
an elongated flat plate;
four writing implements parallel to the plate, on opposite sides and opposite ends of the plate, with two writing implements on each side of the plate, and two writing implements on each end of the plate; and
two legs, each extending in the same direction from one of the two ends of the plate, said legs being at right angles to the plate and coplanar with the plate, with each leg passing between two of the writing implements.

2. The marking device according to claim 1, further comprising:
feet at the end of each leg away from the plate, said feet being made of a softer material than the plate.

3. The marking device according to claim 2, further comprising:
arms that retain the writing implements, said arms extending in opposite directions from each leg at right angles to the plate and the legs.

4. The marking device according to claim 3, wherein:
the writing implements are pencil lead holders.

5. The marking device according to claim 4, further comprising:
knobs on each pencil lead holder, that can be rotated to adjust the position of pencil leads in the pencil dead holders.

6. The marking device according to claim 5, wherein:
the distance of the axis of each pencil lead holder from the closest side of the foot adjacent to the pencil lead holder is marked on the plate adjacent to the pencil lead holder.

7. A marking device comprising:
an elongated flat plate;
two writing implements parallel to the plate, on an end of the plate, with one of the writing implements on each opposite side of the plate; and
a leg extending from the same end of the plate as the writing implements, said leg being at right angles to the plate and coplanar with the plate, with the leg passing between the writing implements.

8. The marking device according to claim 7, further comprising:
a foot at the end of the leg away from the plate, said foot being made of a softer material than the plate.

9. The marking device according to claim 8, further comprising:
arms that retain the writing implements, said arms extending in opposite directions from the leg at right angles to the plate and the leg.

10. The marking device according to claim 9, wherein:
the writing implements are pencil lead holders.

11. The marking device according to claim 10, further comprising:
knobs on each pencil lead holder, that can be rotated to adjust the position of pencil leads in the pencil lead holders.

12. The marking device according to claim 11, wherein:
the distance of the axis of each pencil lead holder from the closest side of the foot adjacent to the pencil lead holder is marked on the plate adjacent to the pencil lead holder.

13. A method of marking teeth, comprising the steps of:
grasping an elongated flat plate with a plurality of writing implements parallel to the plate, said writing implements being on one or more ends of the plate, with one or more of said writing implements on each opposite side of the plate;
placing a leg extending from the same end of the plate as one or more of the writing implements against one or more teeth, said leg being selected from one or more legs, with each of the legs at right angles to the plate and coplanar with the plate, with the legs passing between the writing implements;
pulling one of the writing implements across the object using the flat plate, marking the teeth with a line; and
using the line to position a bracket of an orthodontic brace.

14. The method of marking teeth according to claim 13, wherein:
there are four of the writing implements on opposite sides and opposite ends of the plate, with two writing implements on each side of the plate, and two writing implements on each end of the plate; and
there are two of the legs, each extending in the same direction from one of the two ends of the plate.

15. The method of marking teeth according to claim 13, wherein:
there are two of the writing implements on one end of the plate, with one writing implement on each side of the plate; and
there is only one of the legs.

16. The method of marking teeth according to claim 13, wherein:
there is a foot for each of the one or more legs, with the foot at the end of the leg away from the plate, said foot being made of a softer material than the plate.

17. The method of marking teeth according to claim 16, wherein:
   there are arms that retain the writing implements, said arms extending in opposite directions from each of the legs at right angles to the plate and the leg.

18. The method of marking teeth according to claim 17, wherein:
   the writing implements are pencil lead holders.

19. The method of marking teeth according to claim 18, wherein:
   there are knobs on each pencil lead holder, that can be rotated to adjust the position of pencil leads in the pencil lead holders.

20. The method of marking teeth according to claim 19, wherein:
   the distance of the axis of each pencil lead holder from the closest side of the foot adjacent to the pencil lead holder is marked on the plate adjacent to the pencil lead holder.

\* \* \* \* \*